(12) United States Patent
Ishida et al.

(10) Patent No.: US 7,310,550 B2
(45) Date of Patent: Dec. 18, 2007

(54) ELECTROCARDIOGRAPH AND DISPLAY METHOD FOR ELECTROCARDIOGRAPH

(75) Inventors: Junichi Ishida, Kyoto (JP); Norihito Yamamoto, Otsu (JP); Kazuhisa Tanabe, Kyoto (JP); Yoko Moroki, Kyoto (JP); Masahiro Umeda, Kyoto (JP)

(73) Assignee: Omron Healthcare Co., Ltd., Kyoto-Shi (JP)

( * ) Notice: Subject to any disclaimer, the term of this patent is extended or adjusted under 35 U.S.C. 154(b) by 77 days.

(21) Appl. No.: 10/865,273

(22) Filed: Jun. 10, 2004

(65) Prior Publication Data

US 2005/0004487 A1   Jan. 6, 2005

(30) Foreign Application Priority Data

Jun. 13, 2003   (JP) ............................. 2003-168631

(51) Int. Cl.
  *A61B 5/44*   (2006.01)
(52) U.S. Cl. ................ 600/523; 600/509; 600/525; 345/659; 345/689
(58) Field of Classification Search ................ 600/509, 600/523, 525; 345/659, 689; A61B 5/044
See application file for complete search history.

(56) References Cited

U.S. PATENT DOCUMENTS 4,606,352 A * 8/1986 Geddes et al. .............. 600/515
4,896,677 A    1/1990 Kaneko et al.
6,163,722 A * 12/2000 Magin ............................ 607/5
6,982,728 B1 * 1/2006 Nicolas et al. ............... 345/649
2003/0097078 A1   5/2003 Maeda

FOREIGN PATENT DOCUMENTS

JP    1-502087 A    7/1989
JP    03-012129 A   1/1991

* cited by examiner

*Primary Examiner*—Kennedy J. Schaetzle
*Assistant Examiner*—Natasha Patel
(74) *Attorney, Agent, or Firm*—Baker & Daniels LLP (57) ABSTRACT

A portable electrocardiograph having a display function and method is disclosed. In measuring an electrocardiographic waveform, an electrocardiograph (1) is held in position by a grip including a negative electrode (14) while simultaneously pressing a contact section including a positive electrode (16) against an electrode contact portion other than the right hand of the subject. The measurement result is displayed on a display unit (10) during the measurement operation. The measurement method is divided into the induction mode I in which the contact section including the positive electrode (16) is pressed against the subject's left hand, and the induction mode II in which the contact section including the positive electrode (16) is pressed against the subject's lower left abdomen. In induction mode I, the measurement result is displayed horizontally on the display (10), while in the measurement in mode II, the measurement result is displayed vertically.

2 Claims, 9 Drawing Sheets

ELECTROCARDIOGRAPH AND DISPLAY METHOD FOR ELECTROCARDIOGRAPH

BACKGROUND OF THE INVENTION

1. Field of the Invention

The present invention relates to an electrocardiograph and a display method for the electrocardiograph, and in particular to a portable electrocardiograph having a display function and a display method for the portable electrocardiograph in which the image on display can be easily viewed.

2. Description of the Related Art

An electrocardiogram is used as an effective method of diagnosing heart diseases such as myocardial infarct, angina cordis and ischemic heart disease. In order to diagnose these heart diseases more effectively, the use of the electrocardiogram at the time of occurrence of an abnormality such as a chest pain or palpitation in daily life is desirable for early identification and proper treatment of such diseases. For this reason, there is presently a technique called a 24-hour electrocardiograph, in which the electrocardiographic waveform measured and obtained from the induction electrodes worn for 24 hours by the subject is recorded in a recording device.

The measurement of the electrocardiographic waveform using the 24-hour electrocardiograph, however, imposes a considerable burden on the subject, and it may happen that no abnormality occurs during the measured 24-hour period. In recent years, therefore, a portable electrocardiograph has been proposed to measure the electrocardiographic waveform positively at the time of an abnormality with little burden on the subject, thereby making it possible to measure the electrocardiographic waveform when an abnormality occurs.

This electrocardiograph recently used, as described in Japanese Unexamined Patent Publication No. 1-502087 (hereinafter referred to as Reference 1), has a display on the body of the electrocardiograph to check the measurement in situ.

In measuring the electrocardiographic waveform by holding a grip of the electrocardiograph body including one of the induction electrodes by hand while bringing the other induction electrode into contact with the breast or abdomen constituting an electrode contact portion, however, the direction of the measurement result (graph) displayed on the display may fail to coincide with the direction in which the subject in measurement position can visually check the display, thereby sometimes posing the problem that the image on display is hard to observe. Changing the position to facilitate observation, however, may disrupt the measurement position and make correct measurement impossible.

SUMMARY OF THE INVENTION

This invention has been developed in view of these problems, and the object thereof is to provide a portable electrocardiograph having a display function and a display method for the electrocardiograph in which the image on display can be easily observed visually.

In order to achieve the object described above, according to one aspect of the invention, there is provided an electrocardiograph comprising at least a pair of induction electrodes adapted to be brought into contact with the body of the subject for measuring his/her electrocardiographic waveform, a display for displaying the information and a control means for controlling the direction in which the information displayed on the display is controlled.

Preferably, the information displayed on the display is guide information to guide the user to perform the measuring operation correctly and the control means controls the direction of display in accordance with the measurement position of the subject at the time of measurement.

Also, preferably, the information displayed on the display is an electrocardiographic waveform of the subject measured in the measurement session, and the control means controls the direction of display in accordance with the measurement position of the subject.

Further, preferably, the information displayed on the display is an electrocardiographic waveform of the subject measured in the measurement session, and the control means controls the direction of display in accordance with the relative positions of a measuring person and the subject.

Preferably, the electrocardiograph further comprises a setting means for setting the display direction, wherein the control means sets the information displayed on the display in a set display direction.

Preferably, the control means controls the display to display the information in different directions at the time of measurement and other than the measurement time.

Preferably, the pair of the induction electrodes are arranged substantially at the longitudinal ends of an elongate housing, respectively, the display is arranged on the surface of the housing, and the information is displayed at least in both the longitudinal direction and the direction at right angles to the longitudinal direction.

According to another aspect of the invention, there is provided a display method for the electrocardiograph comprising at least a pair of induction electrodes brought into contact with the body of the subject to measure the electrocardiographic waveform of the subject and a display for displaying the information, the method comprising the steps of acquiring the measurement position of the subject at the time of measurement and controlling the display direction of the information on the display in accordance with the measurement position of the subject.

According to still another aspect of the invention, there is provided a display method for the electrocardiograph comprising at least a pair of induction electrodes brought into contact with the body of the subject to measure the electrocardiographic waveform of the subject and a display for displaying the information, the method comprising the steps of determining whether the measurement is to be conducted by the electrocardiograph or not and controlling the display in different display directions at the time of measurement and at other than the measurement time.

DESCRIPTION OF THE PREFERRED EMBODIMENTS

Embodiments of the invention are explained below with reference to the accompanying drawings. In the following description, the same parts or component elements having the same names and functions are designated by the same reference numerals, respectively, and will not be described in detail again.

Figure 1:
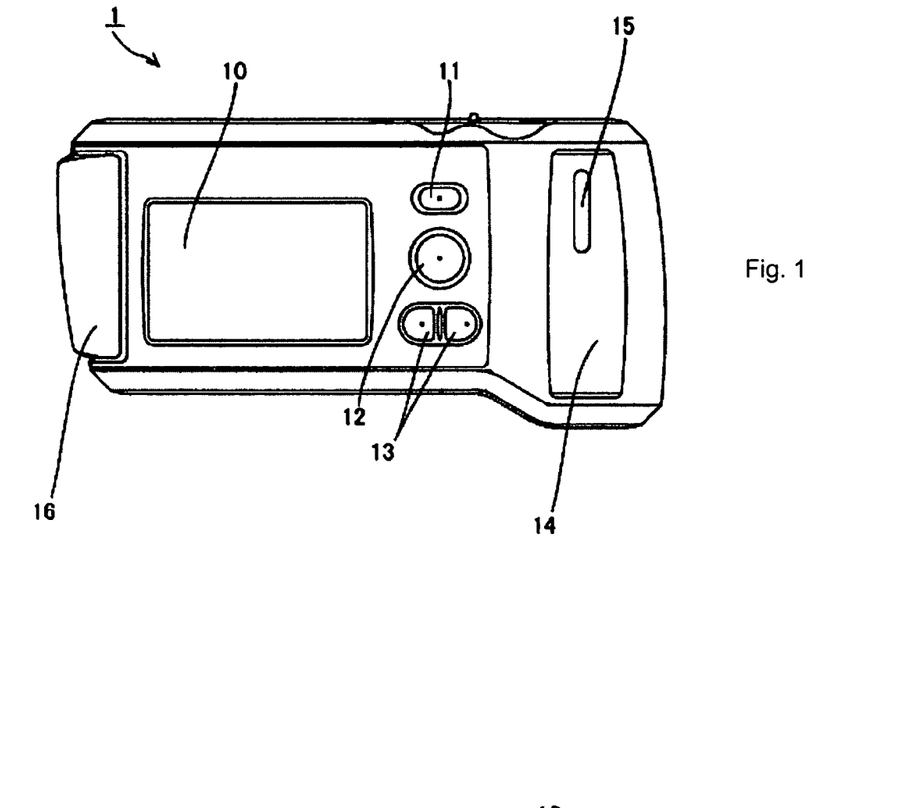
FIG. 1 shows a front view of an electrocardiograph 1.

A specific example of the appearance of a portable electrocardiograph (hereinafter referred to as the electrocardiograph) 1 is shown in FIGS. 1 to 4. The electrocardiograph 1 has a horizontal elongate shape and such a size as to be accommodated in the palm. FIG. 1 is a view of the electrocardiograph 1 taken from the surface having the display and operation functions. By way of explanation, this surface is defined as the front surface and the longitudinal direction as a horizontal direction of the electrocardiograph 1. Specifically, in FIG. 1, the portion to the right on the front surface is defined as the right side of the electrocardiograph 1, and the portion to the left on the front surface as the left side of the electrocardiograph 1. FIG. 1 shows a front view of the electrocardiograph 1, FIG. 2 a top plan view of the electrocardiograph 1, FIG. 3 a left side view of the electrocardiograph 1, and FIG. 4 a right side view of the electrocardiograph 1.

In FIG. 1, the electrocardiograph 1 comprises a display 10 arranged at a position leftward on the front to display the measurement result and the guide information. The electrocardiograph 1 further comprises, on the right side of the display 10, a setting switch 11 used for various settings, a display switch 12 used for displaying the measurement result on the display 10, and a scroll switch 13 for displaying by scrolling the information such as the guide information and the graph of the measurement result displayed on the display 10. Further, on the right side of the front surface of the electrocardiograph 1, there are arranged a negative electrode 14 covering a range corresponding to the vertical side of the electrocardiograph 1 and a protrusion 15 arranged on the negative electrode 14.

Figure 2:
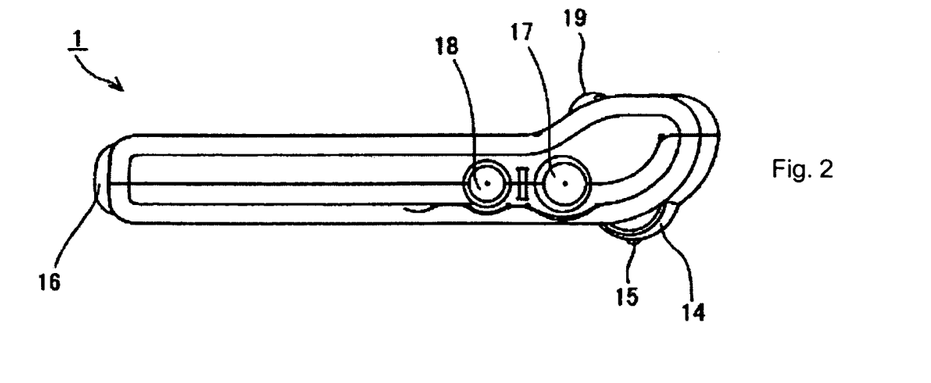
FIG. 2 shows a top plan view of the electrocardiograph 1.
Figure 3:
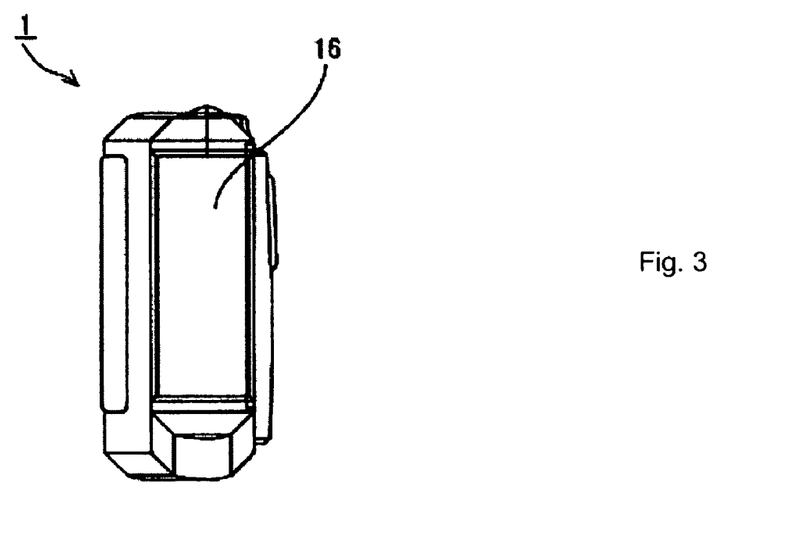
FIG. 3 shows a left side view of the electrocardiograph 1.
Figure 4:
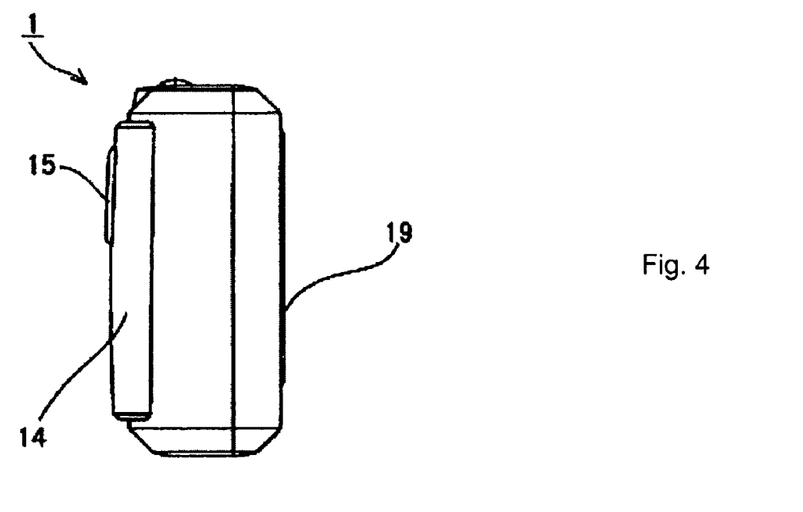
FIG. 4 shows a right side view of the electrocardiograph 1.

In FIGS. 1 to 3, a positive electrode 16 is arranged in a range from the front to the back surface over the left side surface corresponding to the left vertical side of the front.

Further, at a position rightward on the upper surface and leftward of the negative electrode 14 in FIG. 2, there are arranged a measurement switch 17 for starting the measurement and a power switch 18 at the left position adjacent to the measurement switch 17. Also, a neutral electrode 19 constituting an indifferent electrode is arranged on the back surface in the range corresponding to the vertical side in the neighborhood of the position corresponding to the negative electrode 14. The right end portion of the electrocardiograph 1 including the negative electrode 14 and the neutral electrode 19 makes up the grip whereby the particular electrocardiograph 1 is held in the right hand. The left end portion of the electrocardiograph 1 including the positive electrode 16, on the other hand, makes up a contact section by way of which the electrocardiograph 1 is pressed against the electrode contact portion of the subject.

More specifically, the setting switch 11, the display switch 12 and the scroll switch 13 are arranged in such a position as operable by the thumb of the right hand while holding the grip including the negative electrode 14 and the neutral electrode 19 in the right hand. The measurement switch 17 and the power switch 18 are arranged at such a position as operable by the forefinger of the right hand while holding the grip including the negative electrode 14 and the neutral electrode 19 in the right hand. Also, the protrusion 15 is formed to prevent the palm from slipping when the subject holds the grip including the negative electrode 14 and the neutral electrode 19 by the right hand, and intended to bring the negative electrode 14 positively into contact with the right hand of the subject.

Figure 5:
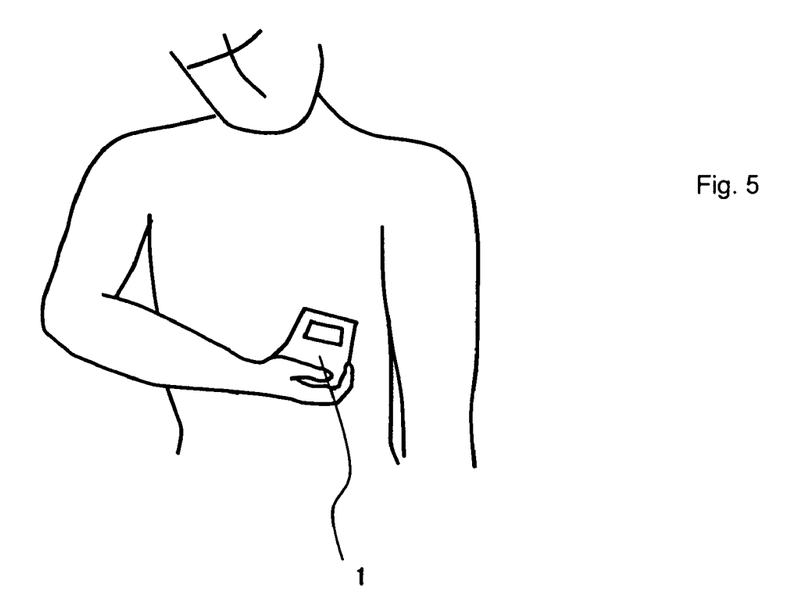
FIG. 5 shows an example of the measurement position.

A specific example of the measurement position of the subject for measuring his/her electrocardiographic waveform using the electrocardiograph 1 according to this embodiment is shown in FIG. 5. Specifically, in FIG. 5, the subject holds the electrocardiograph 1 by the grip including the negative electrode 14 and the neutral electrode 19 of the electrocardiograph 1 in the right hand, and measures the electrocardiographic waveform in a position where the contact section including the positive electrode 16 is pressed against the electrode contact portion other than the right hand of the subject. By doing so, a circuit is formed which reaches the right hand in contact with the negative electrode 14 through the heart from the electrode contact portion in contact with the positive electrode 16. Thus, the action potential (electrocardiographic waveform) caused by the electrical excitation generated at the time of activation of the cardiac muscle of the subject is measured as a potential difference between the positive electrode 16 and the negative electrode 14 constituting the induction electrodes. The measurement method at the position shown in FIG. 5 represents a typical one, in which the negative electrode 14 is contacted by the right hand while the positive electrode 16 is in contact with the skin on the fifth intercostal anterior axillary line.

Figure 6:
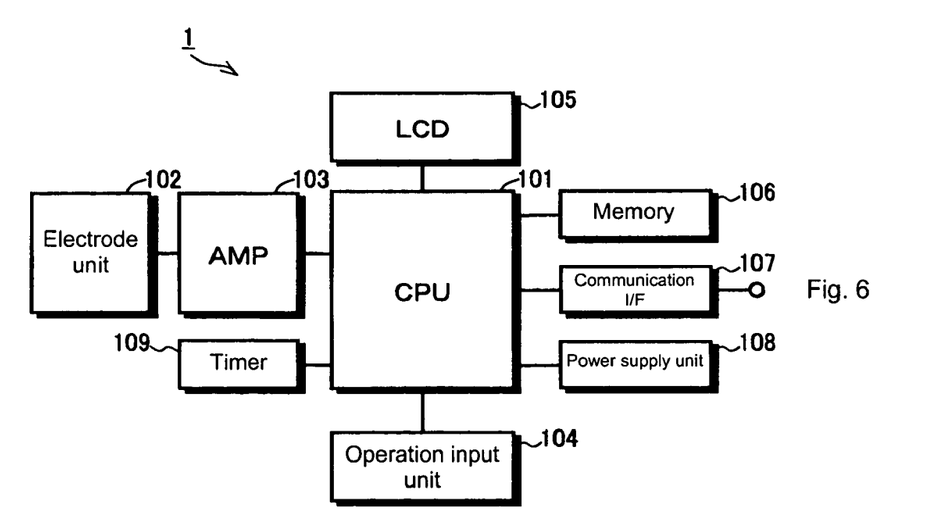
FIG. 6 shows a block diagram of a functional configuration of the electrocardiograph 1.

FIG. 6 is a block diagram showing the functional configuration of the electrocardiograph 1 according to this embodiment. In FIG. 6, the electrocardiograph 1 comprises a CPU (central processing unit) 101, an electrode unit 102 including a positive electrode 16 and a negative electrode 14, an amplifier 103, an operation input unit 104 including switches 11 to 13, 17, 18, a LCD (liquid crystal display) 105 including a display 10, a memory 106 for storing the measurement data and the program executed by the CPU 101, a communication interface (I/F) 107, a power supply unit 108 and a timer 109.

The power supply unit 108 supplies power to the electrocardiograph 1.

Upon activation of the electrocardiograph 1, the CPU 101 reads and executes the program stored in the memory 106 in accordance with the switch signal input from the operation input unit 104, and outputs a control signal to each part of the electrocardiograph 1 thereby to control the overall operation.

Specifically, once the electrocardiograph 1 is activated, the CPU 101 reads the guide screen information stored in the memory 106 and outputs the same information to the LCD 105. The LCD 105 outputs the guide screen input from the CPU 101. As a result, the guide screen is displayed on the display 10.

Also, the CPU 101, upon receipt of a switch signal indicating the depression of the setting switch 11 from the operation input unit 104, reads the setting screen information stored in the memory 106 and outputs the information to the LCD 105. The LCD 105 outputs the setting screen input from the CPU 101. As a result, the setting screen is displayed on the display 10. Further, upon receipt of a switch signal indicating the depression of the scroll switch 13 from the operation input unit 104 under this condition, the setting corresponding to the operation of the scroll switch 13 is stored in a predetermined area of the memory 106.

Also, the CPU 101, upon receipt of a switch signal indicating the depression of the display switch 12 from the operation input unit 104, reads the measurement result stored in the memory 106 and outputs it to the LCD 105. In the case where a data transmission is designated by a transmission switch or the like not shown, the CPU 101, upon receipt of the switch signal indicating the transmission from the operation input unit 104, reads the measurement result stored in the memory 106 and outputs it to an external device through a communication I/F 107. The communication I/F 107 is an interface for serial communication by connecting a cable such as a USB (universal serial bus).

The CPU 101, upon receipt of a switch signal indicating the depression of the measurement switch 17 from the operation input unit 104, outputs a control signal instructing the electrode unit 102 to start the measurement. The CPU 101 also outputs a control signal instructing the timer 109 to start the counting operation.

The electrode unit 102, upon receipt of a control signal from the CPU 101, detects the potential difference between the positive electrode 16 and the negative electrode 14, and outputs an electrode signal representing the detected potential difference to the amplifier 103. The amplifier 103 amplifies the electrode signal input from the electrode unit 102 up to a predetermined amplitude. Also, the amplifier 103 removes noises from the input electrode signal, and outputs the resultant electrode signal to the CPU 101.

The CPU 101 stores the electrode signal input from the amplifier 103 in a predetermined area of the memory 106. Also, the CPU 101 processes the electrode signal input from the amplifier 103 for display thereby to generate a measurement result screen including the electrocardiographic waveform and to output it to the LCD 105. The LCD 105 outputs the measurement result screen input from the CPU 101. In this way, the measurement result screen including the electrocardiographic waveform is displayed on the display 10.

Also, the CPU 101 analyzes the electrode signal input from the amplifier 103, and outputs the message information to the LCD 105 to display a message corresponding to the analysis result on the display 10. In the case where comparison between the electrode signal input from the amplifier 103 and a threshold shows that the electrode signal is different from the threshold by at least a predetermined value, for example, a message indicating the fact may be displayed on the display 10.

The CPU 101 carries out the measurement with the electrode unit 102 until the lapse of a predetermined time length based on the count on the timer 109, and displays the measurement result on the display 10 in real time.

Figure 7:
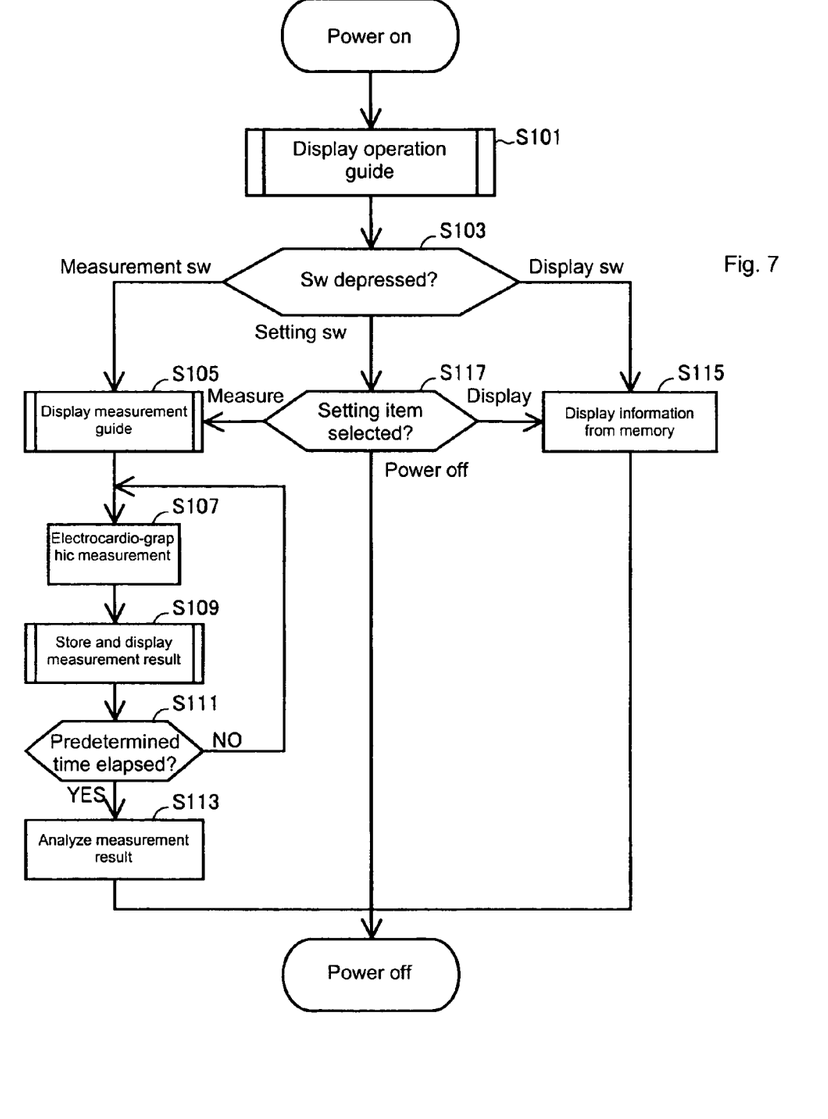
FIG. 7 shows a flowchart showing the process executed in the electrocardiograph 1.

Next, the process executed in the electrocardiograph 1 is explained with reference to the flowchart of FIG. 7. The process shown in the flowchart of FIG. 7 is executed in the case where the electrocardiograph 1 is powered on by depressing the power switch 18. The CPU 101 of the electrocardiograph 1 reads and executes the program stored in the memory 106 thereby to control the various parts shown in FIG. 6.

In FIG. 7, when the electrocardiograph 1 is switched on, the CPU 101 reads the operation guide information from the memory 106 for guiding the user on the operation in general of the electrocardiograph 1. The operation guide information thus read is output to the LCD 105 and displayed on the display 10 (S101). When the user depresses one of the switches in accordance with the operation guide thus displayed, a switch signal corresponding to the particular switch is output from the operation input unit 104 to the CPU 101. The CPU 101 determines which of the switches has been depressed, based on the switch signal input from the operation input unit 104 (S103).

In the case where it is determined in step S103 that the measurement switch 17 is depressed (MEASUREMENT SW in S103), the CPU 101 reads from the memory 106 the measurement guide information to guide the user on the measurement operation, which is output to the LCD 105 and displayed on the display 10 (S105). The CPU 101, after confirming that the subject has brought the negative electrode 14 and the positive electrode 16 correctly into contact with the right hand and the electrode contact portion, respectively, in accordance with the measurement guide, starts the measurement of the electrocardiographic waveform in the electrode unit 102 (S107). The CPU 101 processes the electrode signal received from the electrode unit 102 through the amplifier 103 to obtain the measurement result, and stores the measurement result in a predetermined area of the memory 106. Also, the measurement result is output to the LCD 105 and displayed on the display 10 (S109). In step S109, the electrocardiographic waveform is displayed in real time during the measurement.

The CPU 101 executes the process of steps S107 and S109 for a predetermined time length to measure the electrocardiographic waveform for the predetermined time length. Upon confirming that the predetermined time has elapsed by referring to the timer 109 (YES in S111), the CPU 101 analyzes the measurement result obtained (S113). In step S113, the heart pulsation rate is calculated and the fluctuation of the heart pulsation rate is preferably displayed in graph (R-R graph). Also, preferably, the comments based on the measured waveform are read from a predetermined area of the memory 106 and displayed on the display 10. After that, the process in the electrocardiograph 1 is ended and power is turned off.

After the process in step S113, the CPU 101 may return the process to step S101.

Upon depression of the display switch 12 in step S103 (DISPLAY SW in S103), the CPU 101 reads the measurement result information from a predetermined area of the memory 106, which is output to the LCD 105 and displayed on the display 10 (S115). At the end of the display session, the process in the electrocardiograph 1 is completed and power is turned off.

In the case where the setting switch 11 is depressed in step S103 (SETTING SW in S103), on the other hand, the CPU 101 reads the setting screen information from a predetermined area of the memory 106 and outputs it to the LCD 105 thereby to display a setting screen (not shown) on the display 10. The setting screen includes a measurement button for executing the measurement process in the electrocardiograph 1, a display button for displaying the previous measurement result and a power-off button for turning off the power. The screen of the display 10 can be set by use of the scroll switch 13.

In the case where the measurement button is selected on the setting screen (MEASUREMENT in S117), the CPU 101 proceeds to step S105 and executes a series of the process including steps S105 to S113 for measurement of the electrocardiographic waveform. In the case where the display button is selected on the setting screen (DISPLAY in S117), on the other hand, the CPU 101 passes the process to step S115 to display the measurement result on the display 10. Also, in the case where the power-off button is selected on the setting screen (POWER OFF in S117), the CPU 101 terminates the process in the electrocardiograph 1 and switches off power.

After executing the process of step S113 or step S115, the CPU 101 may detect the depression of the power switch 18 and may turn off power. As another alternative, upon detection of the depression of the setting switch 11, the display switch 12 or the measurement switch 17, the process may proceed to step S117, S115 or S105, respectively, corresponding to each switch.

Figure 8:
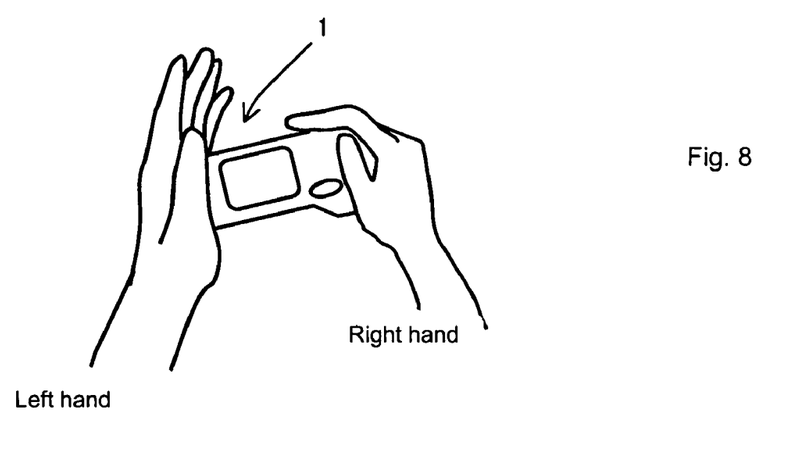
FIG. 8 shows the measurement position of induction mode I.
Figure 9:
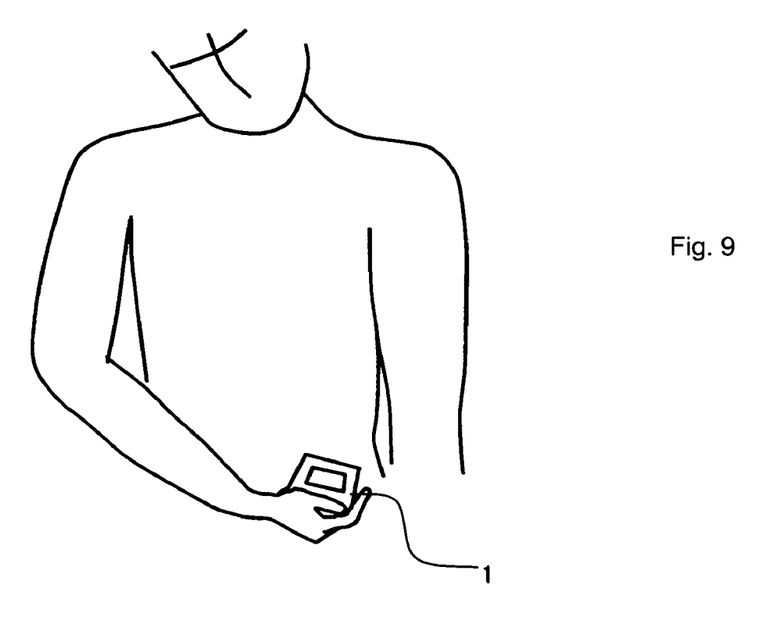
FIG. 9 shows the measurement position of induction mode II.

The position for measuring the electrocardiographic waveform using the electrocardiograph 1 includes, in addition to the position shown in FIG. 5, the position in which as shown in FIG. 8, the subject holds the electrocardiograph 1 by the grip including the negative electrode 14 and the neutral electrode 19 in the right hand while at the same time pressing the contact section including the positive electrode 16 against his/her left hand, or the position in which as shown in FIG. 9, the subject holds the electrocardiograph 1 by the grip including the negative electrode 14 and the neutral electrode 19 in the right hand while at the same time pressing the contact section including the positive electrode 16 against the lower left portion of his/her abdomen. Generally, the manner of the contact arrangement of the induction electrodes in which as shown in FIG. 8, the negative electrode is brought into contact with the right hand and the positive electrode with the left hand is referred to as induction mode I, while the manner of the contact arrangement of the induction electrodes in which as shown in FIG. 9, the negative electrode is brought into contact with the right hand while the positive electrode with the lower left portion of the abdomen instead of the left hand is referred to as induction mode II. With the electrocardiograph according to this invention, a measurement method is employed in accordance with any of the measurement positions of the subject described above.

Any of these measurement methods is set by the user on the setting screen before measurement. Specifically, the setting switch 11 is depressed in step S103 to display the setting screen on the display 10, and the measurement method is set on the setting screen. The CPU 101 accepts the setting by receiving a switch signal from the operation input unit 104 and stores it in a predetermined area of the memory 106. In subsequent measurement sessions, the particular setting is read from the memory 106 automatically as a default measurement method.

Figure 10:
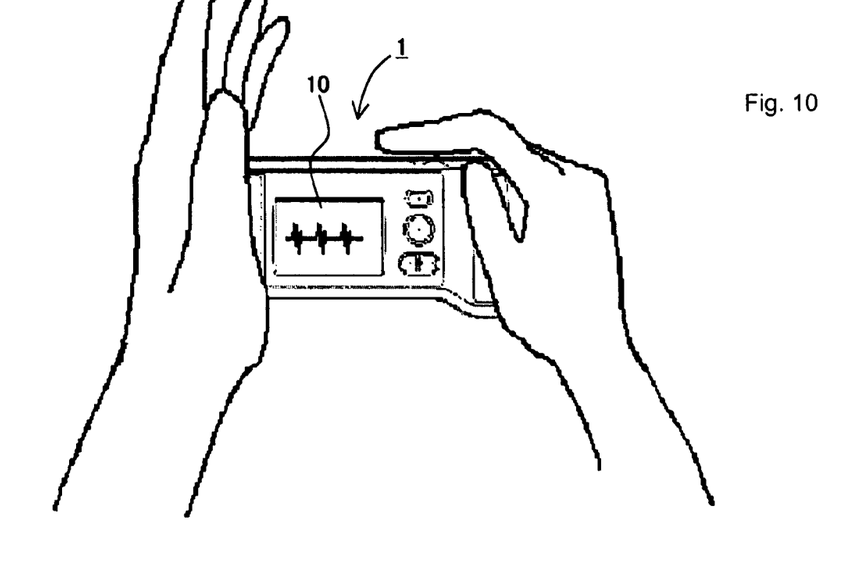
FIG. 10 shows a specific example of the direction (horizontal direction) in which the measurement result is displayed on the display 10.
Figure 11:
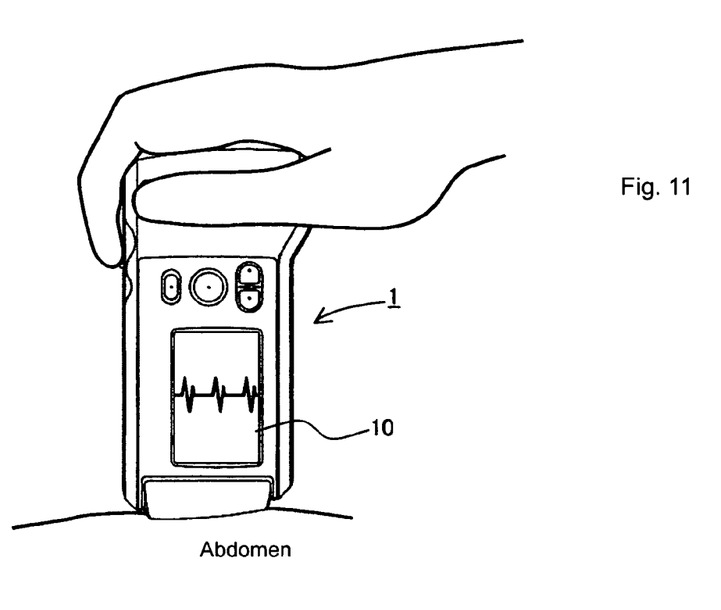
FIG. 11 shows another specific example of the direction (vertical direction) in which the measurement result is displayed on the display 10.

The electrocardiograph 1 according to this embodiment has the feature that in accordance with the difference in the measurement method, i.e. the measurement position of the subject, the direction in which the measurement result is displayed on the display 10 in step S109 can be changed in the manner shown in FIGS. 10 and 11. For convenience' sake, the position of the electrocardiograph 1 arranged horizontally in such a direction that the display 10 is visible from the front is defined as the "horizontal position". In other words, the display position shown in FIG. 10 is called the horizontal position, and the graph shown on the display 10 of FIG. 10 is read from left to right in horizontal direction of the electrocardiograph 1. The display position shown in FIG. 11, on the other hand, is defined as the "vertical position", and the graph shown on the display 10 of FIG. 11 is read top down in the vertical direction of the electrocardiograph 1. Also, characters such as a message, if any, displayed together with the graph on the display 10, are displayed and read in the same direction as shown in FIG. 10 or 11, respectively.

Figure 12:
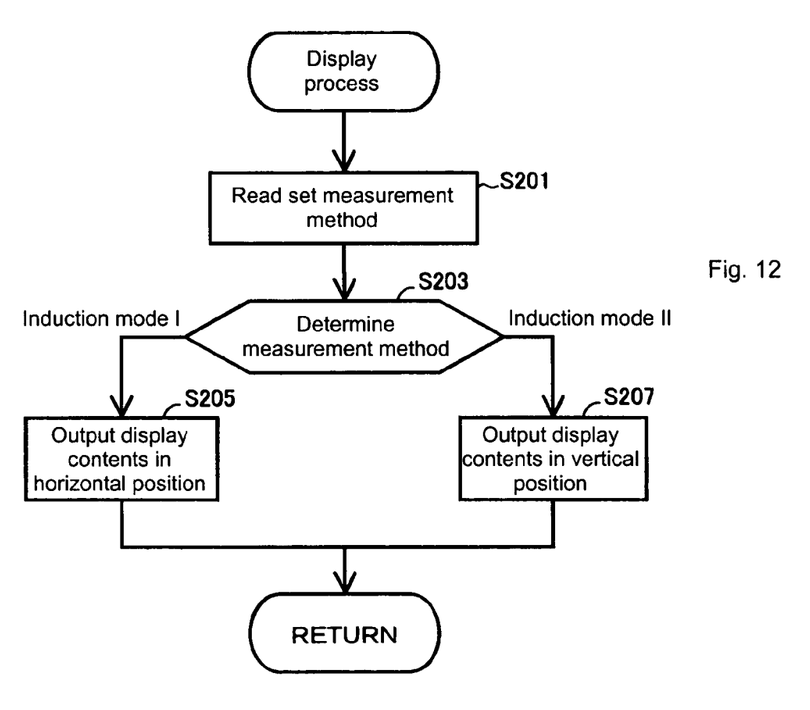
FIG. 12 shows a flowchart showing the display process executed in the electrocardiograph 1.

The display process in step S109 is explained below with reference to the flowchart of FIG. 12.

Assume that the measurement result is processed in step S109. In FIG. 12, the CPU 101 reads the setting of the measurement method from a predetermined area of the memory 106 (S201), and determines whether the setting belongs to induction mode I or induction mode II (S203). In the case where the measurement method belongs to induction mode I ("INDUCTION MODE I" in S203), the measurement result is output in horizontal position to the LCD 105 (S205) and displayed in horizontal position on the display 10. In the case where the measurement method belongs to induction mode II ("INDUCTION MODE II" in S203), on the other hand, the measurement result is output in vertical position to the LCD 105 (S207) and displayed in vertical position on the display 10. In controlling the display position in steps S205, S207, either the measurement result information may be generated in such a manner as to be displayed in horizontal or vertical position and output to the LCD 105, or the attribute for display in horizontal or vertical position may be output to the LCD 105 together with the measurement result information.

By doing so, the measurement result is displayed in real time in horizontal position on the display 10 as shown in FIG. 10 during the measurement according to induction mode I, while the measurement result is displayed in real time in vertical position on the display 10 as shown in FIG. 11 during the measurement according to induction mode II. As a result, the subject can confirm the measurement result displayed on the display 10 in real time without altering his/her measurement position during the measurement process, and thus can obtain the correct measurement result.

Figure 13:
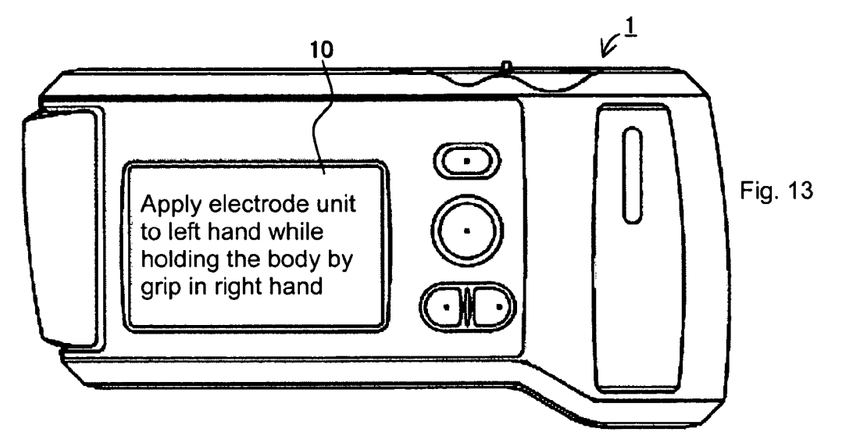
FIG. 13 shows a specific example of the direction (horizontal direction) in which the measurement guide is displayed on the display 10.
Figure 14:
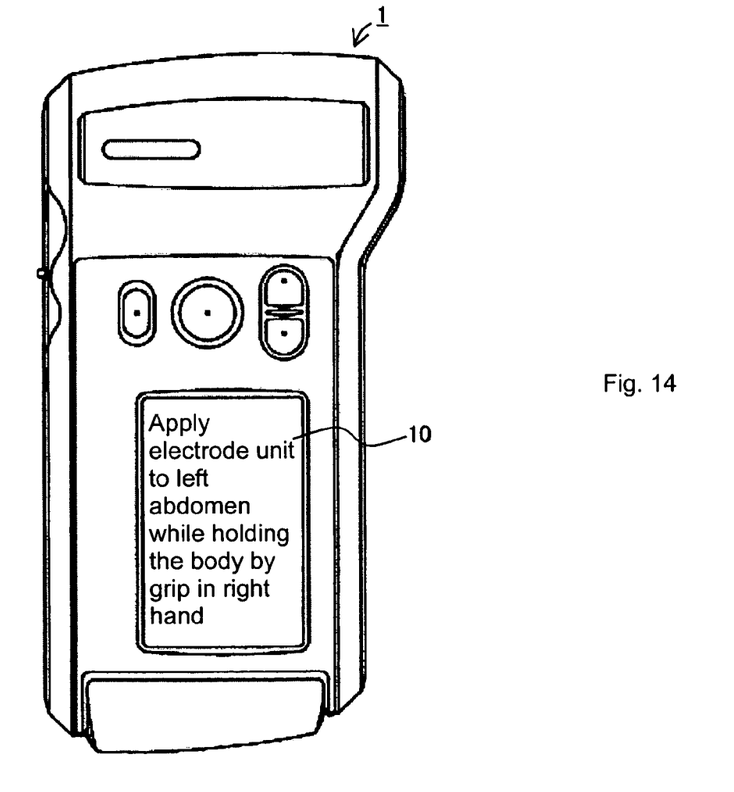
FIG. 14 shows another specific example of the direction (vertical direction) in which the measurement guide is displayed on the display 10.

This display process is preferably executed not only in step S109 described above but also for displaying the operation guide in step S101 or the measurement guide in step S105 as well. Specifically, in step S105, the CPU 101 reads the setting from a predetermined area of the memory 106, and in the case where the particular setting belongs to induction mode I, the measurement guide is displayed in horizontal position as shown in FIG. 13, while in the case of induction mode II, the measurement guide is displayed in vertical position as shown in FIG. 14. In this way, the subject, while watching the measurement guide on the display 10, can press the contact section including the positive electrode 16 against the electrode contact portion by changing the position of the electrocardiograph 1 in such a manner that the measurement guide is displayed adaptively in horizontal position. The subject can thus take a correct measurement position.

According to this embodiment, the measurement method (induction mode I, induction mode II) corresponding to the measurement position can be set by the user in advance, and in accordance with this setting, the guide or the measurement result is displayed in the proper direction. In the case where the electrocardiograph 1 is equipped with the function of detecting the measurement method automatically, however, the operation guide or the measurement result may be adapted to be displayed in the direction corresponding to the measurement method detected.

Figure 15:
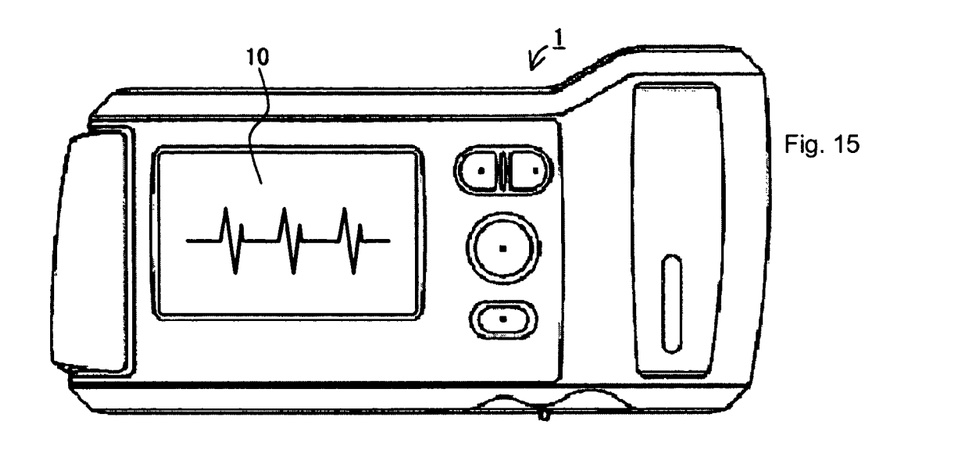
FIG. 15 shows a specific example of the direction in which the measurement result is displayed on the display 10.
Figure 16:
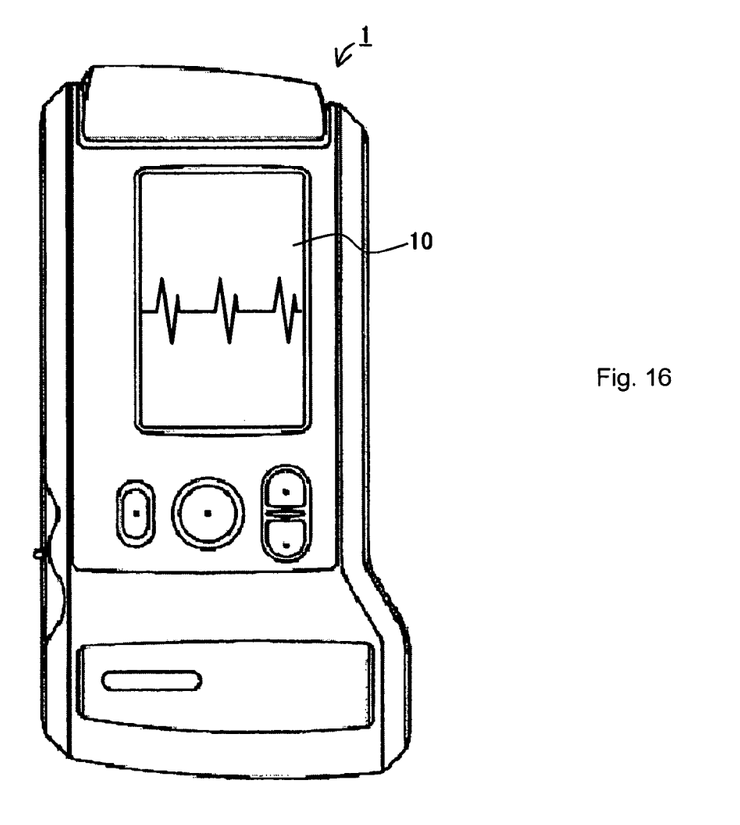
FIG. 16 shows another specific example of the direction in which the measurement result is displayed on the display 10.

The foregoing description has dealt with the case in which the subject himself measures the electrocardiographic wave using the electrocardiograph 1. Nevertheless, the electrocardiograph 1 according to the invention can be used by a measuring person to measure the electrocardiographic wave of the subject. In the latter case, in step S109, as the measurement result is shown in FIG. 15, the display of the electrocardiograph 1 is preferably turned by 180 degrees from the "horizontal position" in FIG. 10, or as shown in FIG. 16, 180 degrees from the "vertical position" shown in FIG. 11. In this way, the display screen of the display 10 of the electrocardiograph 1 is preferably variable by 180 degrees as well as 90 degrees in each direction from the "horizontal position" or the "vertical position". In other words, the position of the electrocardiograph 1 is preferably turned to any of four directions. Thus, the screen on the display 10 of the electrocardiograph 1 may be variable in four directions in accordance with the relative positions of the user and the subject. As in the measurement method, the user sets the display position in advance and the setting is stored in a predetermined area of the memory 106, thereby making it possible to implement the display process in the same way as in the case of FIG. 7. As a result, while the subject is measuring the electrocardiographic waveform by pressing the contact section including the positive electrode 16 against the electrode contact portion, the measuring person can confirm in real time the measurement result displayed on the display 10 without altering the measurement position of the subject, thereby making it possible to acquire the correct measurement result.

Further, the angle by which the display unit 10 of the electrocardiograph 1 is turned each time is not limited to 90 degrees but more preferably variable by any arbitrary angle. Thus, instead of or at the same time as the setting of the measurement method, the display direction on the setting screen is set in advance and the setting is stored in a predetermined area of the memory 106, thereby making it possible to implement the display process the same way as in the case of FIG. 7 described above. As a result, the subject can check the measurement result from the best angle on the display 10 without altering his/her measurement position during the measurement operation, and thus can acquire the correct measurement result. Also, the measuring person, while the subject is measuring his/her electrocardiographic waveform by pressing the contact section including the positive electrode 16 against the electrode contact portion, can check the measurement result from an arbitrary position on the display 10 without altering the measurement position of the subject and thus can acquire the correct measurement result.

[Modification]

Assuming that the electrocardiograph 1 according to a modification is used to measure the electrocardiographic waveform mainly in the measurement position shown in FIG. 5 or 9, the display process for the electrocardiograph 1 according to the modification is explained with reference to the flowchart of FIG. 7. Specifically, according to the modification, the CPU 101 reads the operation guide information stored in the memory 106 and outputs it to the LCD 105 in step S101 so as to be displayed in horizontal position on the display 10.

Also in the case where the setting switch 11 is depressed (SETTING SW in S103) or the display switch 12 is depressed (DISPLAY SW in S103) in step S103, the CPU 101 reads the setting screen information or the measurement result information stored in the memory 106 and outputs it to the LCD 105, thereby displaying the information in horizontal position on the display 10.

In the case where the measurement switch 17 is depressed in step S103 (MEASUREMENT SW in S103), on the other hand, the CPU 101 reads the measurement guide information from the memory 106 in step S105 and outputs it to the LCD 105 to be displayed in vertical position on the display 10. After that, the measurement result is displayed in vertical position on the display 10 in step S109 under the control of the CPU 101.

The method of controlling the direction of display according to the modification is similar to that for the control method described above and therefore is not described again.

As the result of this process executed in the electrocardiograph 1 according to the modification, the measurement guide or the measurement result are displayed in vertical position on the display 10 in accordance with the measurement position when the electrocardiograph 1 is used for measurement, while the information is displayed in horizontal position on the display 10 when the electrocardiograph 1 used for other purposes. Thus, the display operation can be carried out in a way conforming with the position of the electrocardiograph 1 in use for measurement or other purposes. Specifically, at the time of measurement, the electrocardiograph 1 is used in the measurement position shown in FIG. 5 or 9, and therefore the measurement guide or the measurement result is displayed in a direction easy to watch from the particular position. In other than the measurement operation, on the other hand, the electrocardiograph 1 is often used so as to make the longitudinal direction thereof correspond to the horizontal direction, and therefore the operation guide or the previous measurement result is displayed in a direction easy to watch on the electrocardiograph 1 in that position.

Preferably, the angle by which the direction of display can be changed on the display 10 of the electrocardiograph 1 according to the modification is of course not limited to 90 degrees but may be any arbitrary angle.

The embodiments disclosed above should be interpreted as illustrative but not limitative in all respects. The scope of this invention is defined not by the description in the forgoing specification but by the appending claims, and the invention includes all the modifications without departing from the scope and spirit thereof.

For instance, within the scope of the present invention, the electrocardiograph may be designed to be handled and configured for use with by either a right handed or left handed person. Further, the device can be configured for use with two hands or to be administered by a third party. Further, the device can be configured to work with a variety of other devices, such as wireless applications and adapters so that the information measured can be transmitted and displayed on a remote device for further viewing and analysis. Further, the device can be configured to provide a variety of other features and functions.

What is claimed is:

1. An electrocardiograph for measuring electrocardiographic information, the electrocardiograph comprising:

an elongated housing;

a pair of induction electrodes arranged substantially at the elongated ends of the housing;

a display element for displaying the electrocardiographic information; and a control element for controlling the direction in which the information is displayed on the display element;

wherein the control element controls the direction of display in accordance with a measurement method corresponding to a measurement position of a subject;

and further wherein the display element is arranged on a housing surface;

and further wherein the information is displayed on the display element in at least one of the longitudinal direction and the direction perpendicular to the longitudinal direction;

and further wherein a first measurement method comprises contacting a first electrode with a first user hand and a second electrode with a second user hand and the direction of display is a horizontal direction.

2. An electrocardiograph, for measuring electrocardiographic information, the electrocardiograph comprising:

an elongated housing;

a pair of induction electrodes arranged substantially at the elongated ends of the housing;

a display element for displaying the electrocardiographic information; and a control element for controlling the direction in which the information is displayed on the display element;

wherein the control element controls the direction of display in accordance with a measurement method corresponding to a measurement position of a subject;

and further wherein the display element is arranged on a housing surface;

and further wherein the information is displayed on the display element in at least one of the longitudinal direction and the direction perpendicular to the longitudinal direction;

and further wherein a first measurement method comprises contacting a first electrode with a first user hand and a second electrode with a second user hand and the direction of display is a horizontal direction;

and further wherein a second measurement method comprises contacting the first electrode with the first user hand and the second electrode with a user abdomen and the direction of display is a vertical direction.

* * * * *